United States Patent
Day et al.

(10) Patent No.: US 7,547,816 B2
(45) Date of Patent: Jun. 16, 2009

(54) α(1,3)-GALACTOSYLTRANSFERASE KNOCKOUT SWINE, TISSUES AND ORGANS

(75) Inventors: Billy N. Day, Auxvasse, MO (US); Robert J. Hawley, Wayland, MA (US); Randall S. Prather, Rocheport, MO (US)

(73) Assignees: The Curators of the University of Missouri, Columbia, MI (US); Immerge Biotherapeutics, Inc., Cambridge, MA (US)

( * ) Notice: Subject to any disclaimer, the term of this patent is extended or adjusted under 35 U.S.C. 154(b) by 80 days.

(21) Appl. No.: 10/499,407

(22) PCT Filed: Dec. 23, 2002

(86) PCT No.: PCT/US02/41287

§ 371 (c)(1),
(2), (4) Date: Dec. 2, 2004

(87) PCT Pub. No.: WO03/055302

PCT Pub. Date: Jul. 10, 2003

(65) Prior Publication Data

US 2005/0120400 A1   Jun. 2, 2005

Related U.S. Application Data

(60) Provisional application No. 60/343,355, filed on Dec. 21, 2001.

(51) Int. Cl.
*A01K 67/027* (2006.01)
*C12N 15/00* (2006.01)
*A01N 1/00* (2006.01)

(52) U.S. Cl. ............................ 800/17; 800/24; 435/325; 435/1.1; 435/2

(58) Field of Classification Search ........................ None
See application file for complete search history.

(56) References Cited

U.S. PATENT DOCUMENTS

| | | | |
|---|---|---|---|
| 6,153,428 A | 11/2000 | Gustafsson et al. | |
| 6,258,998 B1 | 7/2001 | Damiani et al. | |
| 6,413,769 B1 | 7/2002 | Gustafsson et al. | |
| 6,700,037 B2 * | 3/2004 | Damiani et al. ............... | 800/24 |
| 7,126,039 B2 * | 10/2006 | Denning et al. ............... | 800/17 |
| 2002/0012660 A1 * | 1/2002 | Colman et al. ........... | 424/93.21 |

FOREIGN PATENT DOCUMENTS

| | | |
|---|---|---|
| EP | 0755451 B1 | 5/2005 |
| WO | WO 95/28412 | 10/1995 |
| WO | WO 01/23541 | 4/2001 |
| WO | WO 02/10337 | 2/2002 |
| WO | 02081688 A | 10/2002 |

OTHER PUBLICATIONS

Te Riele et al., "Highly efficient gene targeting in embryonic stem cells through homologous recombination with isogenic DNA constructs," Proc. Natl. Acad. Sci. USA 89: 5128-5132, Jun. 1992.*
Katayama et al, Porcine alpha-1,3-galactosyltransferase: full length cDNA cloning, genomic organization, and analysis of splicing variants, Glycoconjugate J. 15: 583-589, 1998).*
Clark et al. Gene Targeting In Livestock: A Preview. Transgenic Res., 2000, vol. 9, pp. 263-275.*
Denning, "Gene Targeting in Primary Fetal Fibroblasts from Sheep and Pig," 2001, Cloning and Stem Cells, ¾, pp. 221-231.
Ayres et al., "Cloning pigs deficient in alpha 1,3-galactosyltransferase," Graft. Jan./Feb. 2001, vol. 4, No. 1, pp. 80-82.
Betthauser et al., "Production of Cloned Pigs from In Vitro Systems," 2000, Nat. Biotech., 18: 1055-1059.
Bondioli et al., "Cloned pigs generated from cultured skin fibroblasts derived from a H-transferase transgenic boar," Molecular Reproduction and Development. Oct. 2001, vol. 60, No. 2, pp. 189-195.
Costa et al., "Expression of the human alpha 1,2-fucosyltransferase in transgenic pigs modifies the cell surface carbohydrate phenotype and confers resistance to human serum-mediated cytolysis," 1999, FASEB J., 13: 1762-1773.
Dai et al., "Targeted disruption of the alpha 1,3-galactosyltransferase gene gloned pigs," Nature Biotechnology. Mar. 2002, vol. 20, pp. 251-255.
Denning, "Gene Targeting in Primary Fetal Fibroblasts from Sheep and Pig," 2001, Cloning and Stem Cells, ¾: 221-231.
Evans, R.W., "Coming to terms with reality: why xenotransplantation is a necessity." Xenotransplantation, Platt J.L. eds., Washington, DC: ASM Press (2001) 29-51.
Gock et al., "Deleting the Gal epitope from the donor pig," Graft. Jan./Feb. 2001, vol. 4, No. 1, pp. 76-77.
Lai et al., "Production of alpha-1,3-galactosyltransferase knockout pigs by nuclear transfer cloning," Science. 09 Feb. 2002 (online publication), vol. 295, pp. 1089-1092.
Lambrigts D., "Discordant organ xenotransplantation in primates: World Experience and Current Status." 1998, Transplantation, 66:547-561.
McCreath et aol, "Production of gene-targeted sheep by nuclear transfer from cultured somatic cells," 2000, Nature, 405: 1066-1069.
Miyagawa et al., Remodeling of the Major Pig Xenoantigen by N-acetylglucosaminyltransferase III in Transgenic Pig," 2001, J. Biol Chem, 276: 39310-31319.
Park K-W et al.: "Production of nuclear transfer-derived swine that express the enhanced green fluorescent protein," Animal Biotechnology, vol. 12, No. 2, Nov. 2001 92001-11), pp. 173-181.
Petters et al., "Culture of pig embryos," 1993, J. Reprod. Fert. (Suppl) 48:61-73.

(Continued)

*Primary Examiner*—Deborah Crouch
(74) *Attorney, Agent, or Firm*—Senniger Powers LLP

(57) ABSTRACT

The invention relates to the genetic manipulation of non-human animals. More particularly, the invention relates to genetic manipulation of non-human animals to be used for xenotransplantation. The invention provides viable gene knockout swine including swine in which the α(1,3)-galactosyltransferase gene has been disrupted, methods for making such swine, and methods of using the tissues and organs of such swine for xenotransplantation.

18 Claims, 4 Drawing Sheets

OTHER PUBLICATIONS

Phelps et al., "Production of alpha 1,3-galactosyltransferase-deficient pigs," Science. Jan. 17, 2003, vol. 299, pp. 411-414.

Polejaeva et al., "Cloned pigs produced by nuclear transfer from adult somatic cells," Nature Sep. 7, 2000, vol. 407, pp. 86-90.

Sachs et al., "Transplantation in Miniature Swine: I. Fixation of Major Histocompatibility Complex," 1976, Transplantation, 22: 559-567 (1976).

Thall et al., "Oocyte Gal alpha1,3Gal Epitopes Implicated in Sperm Adhesion to the Zona Pellucida Glycoprotein ZP3 Are Not Required for Fertilization in the Mouse," 1995, 270: 21437-21440.

Denning et al., "Deletion of the alpha(1,3) Galactosyl Transferase (GGTA1) Gene and the Prion Protein (PrP) Gene in Sheep," Nature Biotechnology, 2001, 19: 559-562.

Lai et al., "Creating Genetically Modified Pigs by Using Nuclear Transfer," Reproductive Biology and Endocrinology, 2203 1:82, 1-6.

* cited by examiner

α(1,3)-GALACTOSYLTRANSFERASE KNOCKOUT SWINE, TISSUES AND ORGANS

RELATED APPLICATIONS

This application claims priority under 35 U.S.C. 119(e) from U.S. Provisional Application Ser. No. 60/343,355, filed Dec. 21, 2001, which application is incorporated herein by reference.

STATEMENT REGARDING GOVERNMENT RIGHTS

This invention was funded in part by the National Institutes of Health NCRR via R44 RR15198 and NIH DHHS T32 RR07004. The U.S. government has rights in this invention.

FIELD OF THE INVENTION

The invention relates to the genetic manipulation of non-human animals. More particularly, in some embodiments, the invention relates to genetic manipulation of non-human animals to be used for xenotransplantation. For example, this invention provides viable α(1,3)-galactosyltransferase knockout swine, and organs, tissues and cells derived from the knockout swine.

BACKGROUND OF THE INVENTION

Clinical organ transplantation has become one of the major treatments for end-stage organ failure since the introduction of chronic immunosuppressive drugs in the mid 1980s. This success has brought about the secondary issue of limited human organ supply, which greatly limits the ability to provide organs to patients in need of transplants. One of the major approaches to solving this medical need is the utilization of alternative species as a source of organs (xenotransplantation). R. W Evans, in *Xenotransplantation*, J. L. Platt, Ed. (ASM Press, Washington, D.C., 2001), pp. 29-51, teaches that the pig is the primary alternative species due to ethical considerations, breeding characteristics, infectious disease concerns and its compatible size and physiology.

A major barrier to progress in pig-to-primate organ transplantation is the presence of terminal α(1,3) galactosyl (gal) epitopes on the surface of pig cells. Humans and Old World monkeys have lost the corresponding galactosyltransferase activity in the course of evolution and will produce preformed natural antibodies against the epitope that are responsible for hyperacute rejection of porcine organs. The temporary removal of recipient anti-gal antibodies through affinity adsorption and expression of complement regulators in transgenic pigs has allowed survival of transplanted pig organs beyond the hyperacute stage. However, D. Lambrigts, D. H. Sachs, D. K. S Cooper, *Transplantation* 66, 547 (1998), teaches that returning antibody and residual complement activity are likely to be responsible for the acute and delayed damage which severely limits organ survival, even in the presence of high levels of immunosuppressive drugs and other clinical intervention.

Attempts have also been made to prevent rejection by reducing expression of gal epitopes through genetic engineering of the donor animal. Unfortunately, C. Costa et al., *FASEB J.* 13, 1762 (1999), discloses that competitive inhibition of galtransferase in H-transferase transgenic pigs results in only partial reduction in epitope numbers. Similarly, S. Miyagawa et al., *J. Biol. Chem.* 276, 39310 (2001), teaches that attempts to block expression of gal epitopes in N-acetylglucosaminyl-transferase III transgenic pigs also results in only partial reduction of gal epitopes numbers and fails to significantly extend graft survival in primate recipients. Given the large number of gal epitopes present on pig cells, it seems unlikely that any dominant transgenic approach of this nature can provide sufficient protection from anti-gal mediated damage.

A. D. Thall, P. Maly, J. B. Lowe, *J. Biol. Chem.* 270, 21,437 (1995), teaches that viable α(1,3) galactosyltransferase knockout mice can be produced using embryonic stem cell technology. K. L. McCreath et al., *Nature* 405, 1066 (2000), teaches that nuclear transfer (NT) technology can be used for locus specific modification of certain large animals, as demonstrated by the production of viable sheep using in vitro targeted somatic cells. K. W. Park et al., *Anim. Biotech.* 12:173-181 (2001), discloses successful cloning and production of transgenic pigs by nuclear transfer of genetically modified somatic cells. Gustafsson and Sachs, U.S. Pat. No. 6,153,428 (2000), discloses genetically modified porcine cells in vitro in which the α(1,3)-galactosyltransferase gene has been disrupted by homologous recombination. Unfortunately, Bondioli et al., *Mol. Reproduc. Dev.* 60: 189-195 (2001) reports that the attempt to use nuclear transfer technology to accomplish this in pigs in vivo has been unsuccessful.

Therefore, there is a need for a method to generate viable swine with targeted gene knockouts, for example, α(1,3)-galactosyltransferase knockout swine. Such transgenic swine would provide organs, tissues, and cells useful in xenotransplantation.

BRIEF SUMMARY OF THE INVENTION

The invention provides viable knockout swine, including α(1,3)-galactosyltransferase knockout swine and methods for making such swine. The invention also provides organs, tissues, and cells derived from such swine which are useful, for example, in xenotransplantation.

In one embodiment, the invention provides viable α(1,3)-galactosyltransferase knockout swine. Such swine are useful as a source of organs, tissues and cells for xenotransplantation. Such swine are also useful for providing a clearer evaluation of approaches currently in development aimed at overcoming potential delayed and chronic rejection mechanisms in porcine xenotransplantation.

In another embodiment, the invention provides porcine organs, tissues and purified or substantially pure cells obtained from knockout swine that are useful for xenotransplantation. Such porcine organs and tissues lack the α(1,3) galactosyl epitopes that are responsible for hyperacute rejection in primates.

In another embodiment, the invention provides porcine organs, tissues and purified or substantially pure cells obtained from knockout swine that have a decreased expression of gal epitopes, as compared with wild-type swine.

In another embodiment, the invention provides porcine organs, tissues and purified or substantially pure cells obtained from knockout swine that have a decreased expression of functional α(1,3)-galactosyltransferase, as compared with wild-type swine.

In another embodiment, the invention provides tissues that are useful for xenotransplantation. Such tissues lack the α(1,3) galactosyl epitopes that are responsible for hyperacute rejection in primates.

In another embodiment, the invention provides cells that are useful for xenotransplantation. Such cells lack the α(1,3) galactosyl epitopes that are responsible for hyperacute rejection in primates.

In another embodiment, the invention provides a method for making viable swine in which the α(1,3)-galactosyltransferase gene has been disrupted. A method according to this aspect of the invention includes enucleating an oocyte, fusing the oocyte with a donor porcine cell in which a α(1,3)-galactosyltransferase gene has been disrupted to yield an NT-derived embryo, and implanting the NT-derived embryo into a surrogate mother, wherein the surrogate mother has initiated estrus, but has not yet completed ovulation.

In another embodiment, the invention provides a method for making viable swine in which a gene has been disrupted. A method according to this aspect of the invention comprises enucleating an oocyte, fusing the oocyte with a donor porcine cell in which a gene has been disrupted to yield an NT-derived embryo, and implanting the NT-derived embryo into a surrogate mother, wherein the surrogate mother has initiated estrus, but has not yet completed ovulation. In some embodiments, the disrupted gene has been targeted for disruption. In some embodiments, the targeted gene encodes α(1,3)-galactosyltransferase. In some embodiments, the nucleic acid encoding α(1,3)-galactosyltransferase comprises SEQ ID NO:2. In some embodiments, the α(1,3)-galactosyltransferase is SEQ ID NO:1.

In another embodiment, the invention provides viable swine in which a gene has been disrupted. Such swine are useful for studies of gene function and may be particularly useful for determining what genes may be involved in rejection of donor porcine tissues or cells in xenotransplantation.

DETAILED DESCRIPTION OF THE INVENTION

Figure 1:
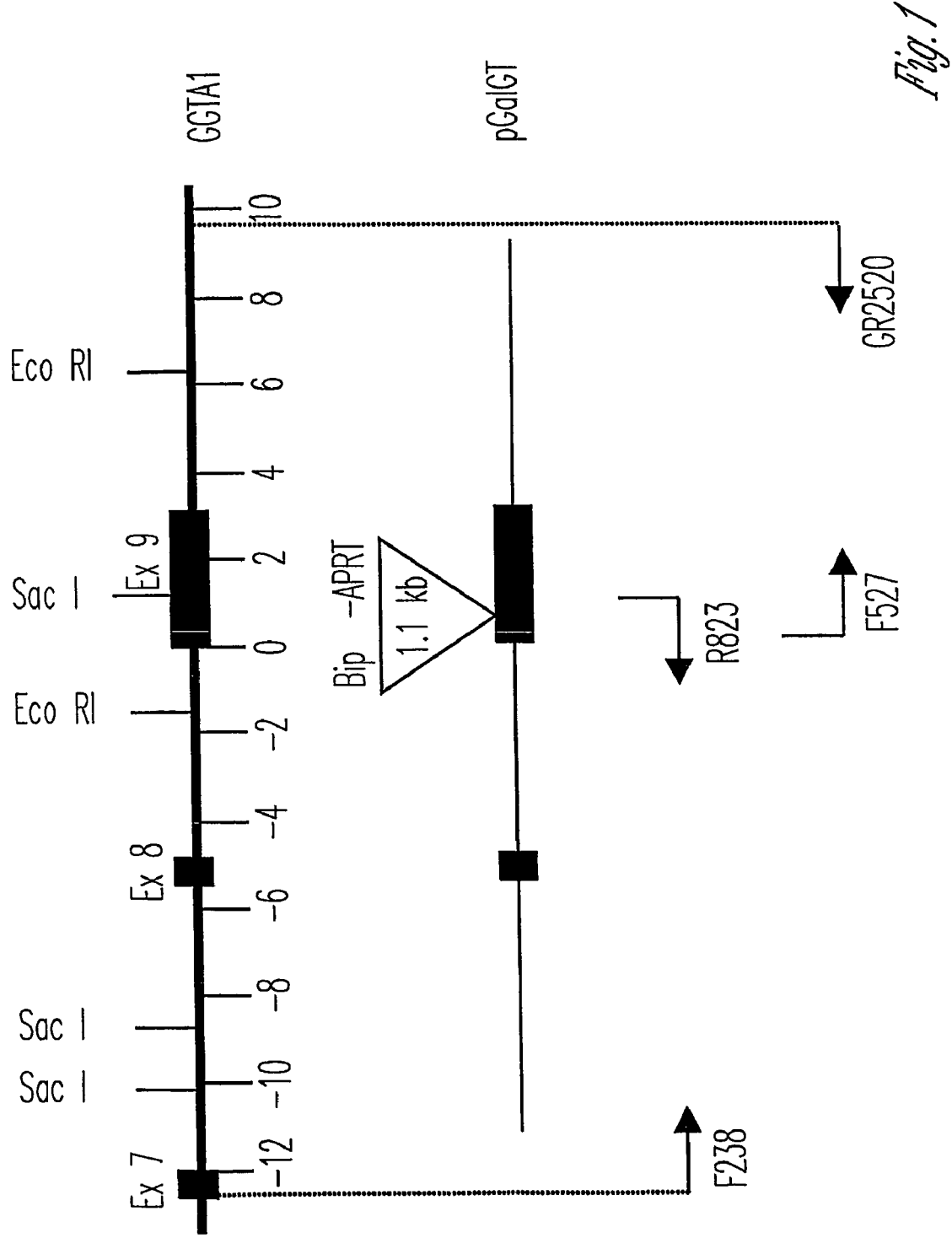
FIG. 1. pGalGT targeting vector and genomic PCR assays for targeting. The structure of the region of the α(1,3)-galactosyltransferase (GGTA1) locus beginning with exon 7 is depicted (scale in kilobase pairs). GGTA1 homologous sequences in the pGalGT vector begin ~0.8 kb downstream of exon 7 and continue to ~6.8 kb downstream of the end of exon 9. A selection cassette, consisting of a Bip internal ribosome entry site, APRT coding sequences (encoding G418 resistance) and flanking stop codons, is inserted into an Eco RV site upstream of the GGTA1 catalytic domain in exon 9. Targeting is assessed using two PCR assays, each incorporating a primer outside of the vector homologous region. Upstream genomic structure is assessed by using primers F238 (exon 7, upstream of the 5' end of the pGalGT vector) and R823 (exon 9 downstream of the selection cassette insertion site). Upon digestion with Eco RI, fragments of 2.0 kb (WT locus), 3.1 kb (targeted locus) and 10.4 kb (either locus) are produced. Downstream genomic structure is assessed by using primers F527 (exon 9 upstream of the selection cassette insertion site) and GR2520 (downstream of the 3' end of the pGalGT vector). Upon digestion with Sac I, fragments of 1.2 kb (WT locus), 2.3 kb (targeted locus) and 8.1 kb (either locus) are produced. A porcine GGTA1 polypeptide is represented in SEQ ID NO:1, and a polynucleotide sequence that encodes SEQ ID NO:1 is provided as SEQ ID NO:2 (see U.S. Pat. No. 6,413,769).

The patents and publications cited herein are hereby incorporated by reference in their entirety. Any inconsistency between the patents and publications and this specification shall be resolved in favor of the latter.

The invention relates to the genetic manipulation of non-human animals. More particularly, the invention relates to genetic manipulation of non-human animals useful for xenotransplantation. The invention provides viable α(1,3)-galactosyltransferase knockout swine, methods for making such swine, and methods of using the cells, tissues and organs of such swine for xenotransplantation.

In one embodiment, the invention provides viable knockout swine. A "knockout swine" is a swine in which the function of one or more alleles of a gene has been altered, for example, by homologous recombination or other insertion or deletion. In certain embodiments, the gene is disrupted. By "disrupted gene" is meant a portion of the genetic code has been altered, thereby affecting transcription and/or translation of that segment of the genetic code, e.g., rendering that segment of the code unreadable through knockout techniques or by insertion of an additional gene for a desired protein or insertion of a regulatory sequence that modulates transcription of an existing sequence. In some embodiments of the invention, all of the cells of the swine include the disrupted gene. In certain embodiments, the knockout swine is a swine in which one or more alleles of the α(1,3)-galactosyltransferase gene has been rendered nonfunctional. In some embodiments, both alleles of the α(1,3)-galactosyltransferase gene are rendered non-functional. Such embodiments include those commonly referred to as "gene knockouts," "gene knock-ins" and any other modification of one or more native allele of the native α(1,3)-galactosyltransferase gene that renders such gene non-functional. Such swine are useful as a source of organs, tissues and cells for xenotransplantation. Such swine are also useful for providing a clearer evaluation of approaches currently in development aimed at overcoming potential delayed and chronic rejection mechanisms in porcine xenotransplantation.

In certain embodiments, the swine is a miniature swine. In certain embodiments, the miniature swine is descendant from the miniature swine disclosed in Sachs et al. *Transplantation* 22, 559 (1976).

In another embodiment, the invention provides porcine organs that are useful for xenotransplantation. Such porcine organs lack the α(1,3) galactosyl epitopes that are responsible for hyperacute rejection in primates. For purposes of the invention, an organ is an organized structure comprising one or more tissues, which organ performs one or more specific biological function. Such organs include, without limitation, heart, liver, kidney, pancreas, lung, thyroid, and skin.

In another embodiment, the invention provides tissues that are useful for xenotransplantation. Such tissues lack the α(1,3) galactosyl epitopes that are responsible for hyperacute rejection in primates. For purposes of the invention, a tissue is an organized structure comprising cells, which tissue, alone or in conjunction with other cells or tissues, performs one or more biological function.

In another embodiment, the invention provides cells that are useful for xenotransplantation. Such cells lack the α(1,3) galactosyl epitopes that are responsible for hyperacute rejection in primates. Such cells are derived from a swine according to the first aspect of the invention. Such cells include, without limitation, Islets of Langerhans cells, blood precursor cells, bone precursor cells, neuronal, and primordial stem cells.

In another embodiment, the invention provides a method for making viable α(1,3)-galactosyltransferase knockout swine. The method according to this aspect of the invention comprises enucleating an oocyte, fusing the oocyte with a donor porcine cell in which a α(1,3)-galactosyltransferase gene has been rendered non-functional to yield an NT-derived embryo, and implanting the NT-derived embryo into the uterus of a surrogate mother, wherein the surrogate mother has initiated estrus, but has not yet completed ovulation.

In certain embodiments, the oocyte is obtained from a gilt. A "gilt" is a female pig that has never had offspring. In certain embodiments, the oocyte is obtained from a sow. A "sow" is a female pig that has previously produced offspring. In certain embodiments, the donor cell is a primary fibroblast. In certain embodiments, the donor cell is fused with the enucleated oocyte. Alternatively, the nucleus of the donor cell can be directly injected into the cytoplasm of the enucleated oocyte. In certain embodiments, the NT-derived embryo is implanted in the uterus of the surrogate mother together with parthenogenetic embryos. In certain embodiments, the NT-derived embryo is implanted in the uterus of the surrogate mother after the surrogate mother has been bred. In some, but not all embodiments, the oocytes are in vitro matured. In some embodiments, the surrogate mother is a gilt. In some embodiments, the surrogate mother is a sow.

In another embodiment, the invention provides a method for making viable swine in which a gene has been disrupted. A method according to this aspect of the invention includes enucleating an oocyte, fusing the oocyte with a donor porcine cell in which a gene has been disrupted to yield an NT-derived embryo, and implanting the NT-derived embryo into a surrogate mother, wherein the surrogate mother has initiated estrus, but has not yet completed ovulation.

In certain embodiments, the oocyte is obtained from a gilt. In certain embodiments, the oocyte is obtained from a sow. In certain embodiments, the donor cell is a primary fibroblast. In certain embodiments, only the nucleus of the donor cell is fused with the oocyte. In certain embodiments, the NT-derived embryo is implanted in the uterus of the surrogate mother together with parthenogenetic embryos. In certain embodiments, the NT-derived embryo is implanted in the uterus of the surrogate mother after the surrogate mother has been bred. In some, but not all embodiments, the oocytes are in vitro matured. In some embodiments, the surrogate mother is a gilt. In some embodiments, the surrogate mother is a sow.

In another embodiment, the invention provides viable swine in which a gene has been disrupted. Such swine are useful for studies of gene function and may be particularly useful for determining what genes may be involved in rejection of donor porcine tissues or cells in xenotransplantation. In certain embodiments, the swine is a miniature swine. In certain embodiments, the miniature swine is descendant from the miniature swine disclosed in Sachs et al., *Transplantation* 22, 559 (1976).

Certain advantageous features of the invention will become evident from the following examples. Under certain growth and selection conditions, miniature swine fetal fibroblasts maintain a steady doubling time of approximately 24 hours. Clonal lines senesce following 30-32 days of culture on average. The ability to quickly select clonal lines for nuclear transfer is likely to be a requirement for introduction of other complex genetic alterations into the pig genome. The ability to use cryopreserved donor cells without further culture, demonstrated by two of the inventors' litters, is also advantageous, as it extends the number of potential donor lines available for use in nuclear transfer. The present efficiencies in producing NT-derived GGTA1 knockout animals are similar to those previously reported (see e.g., J. Betthauser et al., *Nat. Biotechnol.* 18, 1055 (2000); K. Bondioli, J. Ramsoondar, B Williams, *Mol. Reprod. Dev.* 60, 189 (2001)), in which extensively cultured primary fetal cells were used as nuclear donors despite the nearly 4-fold difference in adult size between the miniature swine strain modified here and the commercial oocyte donor and surrogate strains used. The ability to use readily available oocyte donors and surrogates in a nuclear transfer program is essential when modification of less commonly available animals is required. Another advantage is provided by asynchronous embryo transfer. For purposes of the invention asynchronous embryo transfer means transfer of an NT-derived embryo to a surrogate at an earlier stage of the estrus cycle than the NT-derived embryos themselves.

The terms "nucleic acid molecule," "gene," "nucleic acid sequence," "polynucleotide," "construct," and "nucleic acid region," encoding a protein or proteins refer to a nucleic acid sequence that includes a sequence encoding the protein or proteins. The protein can be encoded by a full-length coding sequence, or by any portion of the coding sequence, as long as the desired activity is retained. The coding region may be present either in a cDNA, genomic DNA or RNA form. When present in a DNA form, the nucleotide sequence may be single-stranded (i.e., the sense strand) or double-stranded. Suitable control elements such as enhancers/promoters, splice junctions, polyadenylation signals, etc. may be placed in close proximity to the coding region of the construct if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The following terms are used to describe the sequence relationships between two or more polynucleotides, or polypeptides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a sequence, wherein the sequence in the comparison window may include additions or deletions (i.e., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene,* 73:237 (1988); Higgins et al., *CABIOS,* 5:151 (1989); Corpet et al., *Nucl. Acids Res.,* 16:10881 (1988); Huang et al., *CABIOS,* 8:155 (1992); and Pearson et al., *Meth. Mol. Biol.,* 24:307 (1994). The ALIGN program is based on the algorithm of Myers and Miller, supra. The BLAST programs of Altschul et al., *JMB,* 215:403 (1990); *Nucl. Acids Res.,* 25:3389 (1990), are based on the algorithm of Karlin and Altschul supra.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See http://www.ncbi.nlm.nih.gov. Alignment may also be performed manually by inspection.

For purposes of the present invention, comparison of sequences for determination of percent sequence identity is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, or at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, in some embodiments, at least 80%, in some embodiments at least 90%, and in some embodiments at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide includes a sequence with at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, or even, 95%, 96%, 97%, 98% or 99%, sequence identity to the reference sequence over a specified comparison window. Optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267 (1984); $T_m$ 81.5° C.+16.6 (log M)+0.41 (% GC)−0.61 (% from)−500/L; where M is the molarity of monovalent cations, % GC is the percentage of guanosine and cytosine nucleotides in the DNA, % from is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993). Generally, highly stringent hybridization and wash conditions are selected to be about 5° C. lower than the thermal melting point ($T_m$) for the specific sequence at a defined ionic strength and pH. In some embodiments, a stringent condition includes a washstep of four times SSC at 60° C.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The production of GGTA1 knockout pigs reported here is an important advance for the field of xenotransplantation. α(1,3) galactosyltransferase null pigs, produced from the animals described herein by mating or by sequential nuclear transfer modification, not only eliminate hyperacute rejection but also ameliorate later rejection processes contributed to by antibodies against the gal epitope. In conjunction with clinically relevant immunosuppressive therapy, elimination of gal epitopes permits long term-survival of transplanted porcine organs. At a minimum, availability of galactosyltransferase null pigs allows a clearer evaluation of approaches currently in development aimed at overcoming potential delayed and chronic rejection mechanisms in porcine xenotransplantation.

The terms "pig" and "swine" are generic terms referring to the same type of animal without regard to gender, size, or breed.

The following examples are intended to further illustrate certain embodiments of the invention and are not intended to limit the scope of the invention in any way. Except as otherwise noted, all chemicals are from Sigma (St. Louis, Mo.).

EXAMPLE 1

Generation of Knockout Primary Fetal Porcine Cells

A highly inbred, MHC-defined miniature pig line, descendent from lines long used for xenotransplantation studies was used (see D. H. Sachs et al., *Transplantation* 22, 559 (1976)). This line is an ideal size-match for eventual use in clinical transplantation and has animals that consistently test negative for transmission of porcine endogenous retrovirus (PERV) to human cells.

Cells were isolated from 1 male (F9) and 3 female (F3, F6, F7) fetuses at day 37 of gestation for production of donor cell lines. Primary fibroblasts were isolated by collagenase/trypsin digestion of minced tissue. Dissociated cells were plated at $2 \times 10^5$ cells/cm$^2$ on collagen-coated plates in Ham's F10 medium containing 20% FBS and antibiotics. Adherent cells were frozen the following day.

The fibroblasts were thawed at 37° C., and 200 µl fetal calf serum (FCS) was added. The cells were then cultured for 3 days to subconfluence prior to transfection. A gene trap targeting vector, pGalGT (FIG. 1), was used for homologous replacement of an endogenous GGTA1 allele. The vector contains approximately 21 kilobases of homology to the GGTA1 locus, with the coding region upstream of the catalytic domain disrupted by insertion of a selection cassette consisting of an internal ribosome entry site followed by sequences encoding G418 resistance (APRT).

Approximately $2 \times 10^7$ fibroblasts were electroporated at 260 V, 960 uFD in 0.8 ml of Hepes buffered saline containing 0.5 pmol/ml of pGalGT. The vector was restriction digested at both ends of the GGTA1 homologous sequences prior to use. Transfected cells were cultured in bulk for 2 days without selection, then plated in collagen-coated 96 well plates at $2 \times 10^4$ cells per well in Ham's nutrient mixture F10-20% fetal bovine serum (FBS) containing 100 µg/ml G418. The low selection concentration was made possible by absence of cells transiently expressing G 418 resistance; untransfected cells were uniformly killed by 50-75 µg/ml of G418 after 5-7 days. Following 14 days of selection in G418, growing cultures were passaged in triplicate (Table 1) for cryopreservation of donor cells, RT-PCR screening for targeting, and DNA isolation. Subconfluent donor cell cultures were trypsinized and frozen in aliquots of 1000-2000 cells in 20 µl aliquots.

Cells were plated with G418 selective medium in 96 well plates 2 days following transfection with the pGalGT targeting vector at $2 \times 10^4$ cells/well. Following 14 days of selection, wells containing healthy cells were passaged in triplicate. Stable rate was calculated by dividing the number of wells with growth by the number of transfected cells plated. Clones scored positive in the preliminary RT-PCR analysis were cryopreserved and expanded for genomic DNA analysis. Clones having the predicted upstream and downstream structure for replacement-type targeting (as described in FIG. 1) were scored positive. Five clonal lines senesced before sufficient DNA could be obtained to complete genomic analysis (ND). Among the 9 F6-derived clones that scored negative, 3 gave no evidence of targeting, 1 was positive only in the upstream analysis (possible insertion-type recombination event) and 5 had a targeted allele band of significantly lower intensity than the corresponding wild-type band. Donor isolation rate was calculated by dividing the number of genomic positive clones obtained by the number of transfected cells plated.

TABLE 1

Isolation of GGTA1 knockout donor cell lines.

| Fetal Line | Wells Plated | Clones (1% of wells) | Stable Rate | RT-PCR + (% of clones) | Genomic Positive | Targeting Negative | Analysis ND | Donor Isolation Rate |
|---|---|---|---|---|---|---|---|---|
| F3 | 288 | 18 (6.2%) | $3.1 \times 10^{-6}$ | 2 (11%) | 1 | 0 | 1 | $1.8 \times 10^{-7}$ |
| F6 | 648 | 69 (10.6%) | $5.3 \times 10^{-6}$ | 14 (20%) | 2 | 9 | 3 | $1.5 \times 10^{-7}$ |
| F7 | 552 | 46 (8.3%) | $4.2 \times 10^{-6}$ | 5 (11%) | 4 | 0 | 1 | $3.6 \times 10^{-7}$ |
| F9 | 960 | 26 (2.7%) | $2.7 \times 10^{-6}$ | 1 (4%) | 1 | 0 | 0 | $5.2 \times 10^{-8}$ |
| Total/Avg | 2448 | 159 (6.5%) | $3.2 \times 10^{-6}$ | 22 (14%) | 8 | 9 | 5 | $1.6 \times 10^{-7}$ |

Due to the limited lifespan of primary fetal cells, it was necessary to quickly identify potentially targeted clones. RT-PCR was performed on crude cell lysates the day following passage using a forward primer from exon 7 (upstream of the 5' end of the targeting vector) and a reverse primer from the selection cassette. Lysates were prepared from 96 well cultures of selected clones the day following passage by three rounds of freezing and thawing in 10 µl of 2 mM dithiothreitol containing 1 U/µl placental ribonuclease inhibitor. The lysate was amplified in a one tube amplification reaction using rTth polymerase, exon 7 forward primer F291 (5-ACAACAGAG-GAGAGCTTCCG-3; SEQ ID NO:3) and reverse primer Bip419 (5-CTCTCACACTCGCGAAACAC-3; SEQ ID NO:4). PCR products were alkaline denatured and transferred to nylon membranes prior to hybridization with an exon 8 oligonucleotide probe (5-GGTCGTGACCATAAC-CAGATG-3; SEQ ID NO:5). Dot blot hybridization of the RT-PCR products using an exon 8 probe detected targeting in 22 of 159 clones analyzed (14%). Subconfluent cultures of RT-PCR positive clones were cryopreserved in aliquots of 1000-2000 cells, with a total of 26 days of ex vivo culture following fetal isolation.

Clones identified as putatively targeted in the RT-PCR screening assay were expanded into 24 well plates and DNA isolated for genomic analysis as diagrammed in FIG. 1. The structure of the GGTA1 locus was analyzed in two overlapping PCR reactions. Approximately 250 ng of DNA was amplified in reactions with LA Taq DNA polymerase (Panvera, Madison, Wis.). Upstream analysis utilized exon 7 forward primer F238 (5-TTACCACGAAGAAGAAGACGC-3; SEQ ID NO:6) and exon 9 reverse primer R823 (5-AGGATGTGCCTTGTACCACC-3; SEQ ID NO:7). Reactions were digested with Eco RI prior to electrophoresis on 0.8% agarose gels. Downstream analysis utilized exon 9 forward primer F527 (5-GGTTGGCCACAAAGTCATC-3; SEQ ID NO:8) and reverse primer GR2520 (5-CACTATTTGGAGGACAGGGTC-3; SEQ ID NO:9). Reactions were digested with Sac I and electrophoresed as above. Southern blots of digested reactions were hybridized to IRES region probe Bip419 (see above).

Clones with a targeted insertion of the cassette relative to vector external primer sites both upstream and downstream of the cassette, indicative of a replacement-type targeting event, were considered candidates for use in nuclear transfer. Of 17 clones analyzed, 8 were found to have undergone the desired recombination event and one from each fetus (F3-C5, F6-C3, F7-H6 and F9-J7) was used for nuclear transfer.

EXAMPLE 2

Nuclear Transfer into Enucleated Oocytes

Oocytes derived from slaughtered gilts were matured in defined protein medium (TCM 199 supplemented with 0.1% PVA 0.1 mg/ml cysteine, 10 ng/ml EGF, 0.91 mM Na-pyruvate, 3.05 mM D-glucose, 0.5 µg/ml FSH, 0.5 µg/ml LH, 75 µg/ml penicillin, 50 µg/ml streptomycin). Oocytes from sow ovaries were purchased from BioMed, Inc. (Madison, Wis.) and shipped in maturation medium (TCM 199-Hepes, supplemented with 5 µg/ml insulin, 10 ng/ml EGF, 0.6 mM cysteine, 0.2 mM Na-pyruvate, 3 µg/ml FSH 25 ng/ml gentamycin and 10% porcine follicular fluid) overnight. Porcine follicular fluid was collected from follicles of 3 to 6 mm diameter, centrifuged at 1500×g for 30 minutes at 4° C., filtered through 1.2 µm syringe filters and stored at −20° C. until use. Nuclear transfer was performed using in vitro matured oocytes and, except for 4 transfers noted in Table 2, cryopreserved donor cells without further culture. After 42 to 44 h of maturation, oocytes were freed of cumulus by vigorous pipetting in the presence of hyaluronidase. Oocytes with an intact plasma membrane were selected and kept in TCM 199 supplemented with 4 mg/ml BSA until use. Enucleation of metaphase II oocytes was performed in medium supplemented with 7.5 µg/ml cytochalasin B, without staining the chromatin as this may be detrimental to subsequent development. Cryopreserved donor cells were thawed at 37° C. and 10 volumes of FCS were added. The suspension was kept at room temperature for 30 min. Subsequently, 4 volumes of TCM/BSA was added and the cells were pelleted at 500 g for 5 min. Fibroblast cells were resuspended in 15-20 µl medium and directly used for NT. For NT-derived embryos transferred to four surrogates (O230, O203, O291 and O221) the cells were cultured one week as above, then overnight in medium containing 0.5% serum prior to use in nuclear transfer. All cells with an intact membrane were used, as the limited number of targeted cells did not permit any selection. A single cell was transferred into the perivitelline space with the same pipette used for enucleation. For fusion and activation, cytoplast-fibroblast-complexes were place between 2 electrodes (1 mm apart), overlayed with fusion medium (0.3 M mannitol, 1 mM CaCl$_2$, 0.1 mM MgCl$_2$, 0.5 mM Hepes) and aligned manually. Fusion and activation were achieved simultaneously by 2 pulses of 1.2 kV/cm for 30 µsec as measured by a BTX-optimizer (Biotechnology and Experimental Research, San Diego, Calif.). Embryos were kept in TCM/BSA for another 30-60 min before the fusion rate was evaluated. Fused embryos were cultured in 500 µl NCSU 23 (see Petters and Wells, *J. Reprod. Fert.* Supplement 48:61-73 1993)) supplemented with 4 mg/ml BSA overlayed with mineral oil. The surviving embryos (intact plasma membrane) were selected for transfer into surrogates after culture for 18-22 h.

EXAMPLE 3

Transfer of NT-Derived Embryos to Mated Surrogates

Potential surrogates were checked for estrus twice a day. Depending upon the exact time of estrus, NT-derived embryo transfers were performed 5-17 hours or 20-36 hours following the actual onset of estrus for day 0 and day 1 surrogates, respectively. In prior control experiments using in vitro-produced embryos cultured for 22 hours following fertilization and then transferred to a day 1 surrogate, 19 of 100 embryos recovered on day 6 were at blastocyst stage, with an average nuclear number of 65. For surgery, gilts were pre-anesthetized with Pentothal® (Abbott Laboratories, North Chicago, Ill.) and anesthesia was maintained with 2% Halothane (Halocarbon Laboratories, River Edge, N.J.). A midventral laparotomy was performed, embryos loaded into a tomcat catheter and deposited into the oviduct. Benamine (flunixin meglumine, 1.5 ml IM) was administered to the surrogate during the surgery. Examination of the ovaries during embryo transfer confirmed that none of the surrogates had completed ovulation.

The observed benefit of asynchronous transfer suggests that any manipulation may result in a delay in early embryonic development. Asynchronous embryo transfer, i.e., transfer to a surrogate at an earlier stage of the estrus cycle than the embryos themselves, was employed because the manipulations required for nuclear transfer are quite extensive and may slow development, and the miniature swine embryos of the strain used here may normally develop at a relatively slower rate. Thus, naturally cycling large white gilts that had displayed standing estrus, but had not yet completed ovulation, were used as surrogates. A total of 28 embryo transfers were performed (Table 2).

Sexually mature surrogate gilts were heat checked twice daily for signs of estrus; the first day of standing estrus is designated day 0. Surrogates receiving estradiol on day 12 are indicated (#). Where indicated (*), donor cell lines were cultured for 1 week prior to NT. The number of NT-derived and parthenogenetic embryos transferred is indicated. Parthenogenetic embryos were transferred to surrogates Y155 and O136 on the day of activation; all other embryos were transferred following overnight culture. Surrogates were checked for pregnancy by transabdominal ultrasound examination beginning around day 26 and weekly thereafter; confirmed pregnancies are shaded.

TABLE 2

Transfers of embryos reconstructed with GGTA1 knockout cell line

| Surrogate (estrus day) | Donor Line | Oocytes | NT Embryos | Parth. Embryos | Outcome |
|---|---|---|---|---|---|
| O198 (0) | F3-C5 | Gilt | 85 | 10 | Degenerated day 26-31 |
| 98-1 (1) | F6-C3 | Gilt | 59 | 10 | Degenerated day 27-33 |
| O159 (1) | F6-C3 | Gilt | 47 | 10 | Degenerated day 33-38 |
| Y98 (2) # | F9-J7 | Sow | 143 | 20 | Degenerated day 40-47 |
| O169 (1) # | F9-J7 | Gilt, Sow | 135 | 15 | 1 mummy recovered at term |
| Y227 (1) # | F9-J7 | Sow | 118 | 20 | Return to estrus on day 28 |
| Y117 (1) # | F9-J7 | Sow | 76 | 20 | Return to estrus on day 33 |
| O212 (0) | F7-H6 | Sow | 116 | 0 | Mated surrogate 7 born, 1 NT-derived |
| O226 (1) | F3-C5 | Sow | 92 | 0 | 4 NT-derived piglets born |
| O204 (1) | F3-C5 | Sow | 153 | 0 | Degenerated day 47-53 |
| Y242 (1) | F3-C5 | Sow | 131 | 0 | Return to estrus on day 27 |
| O171 (1) | F3-C5 | Sow | 152 | 0 | Return to estrus on day 25 |
| O202 (1) | F3-C5 | Gilt | 120 | 0 | Return to estrus on day 24 |
| O194 (1) | F3-C5 | Sow | 148 | 0 | Return to estrus on day 32 |
| 94-4 (1) | F6-C3 | Sow | 88 | 0 | Degenerated day 27-33 |
| Y134 (1) | F6-C3 | Sow | 109 | 0 | Return to estrus on day 33 |
| O230 (1) | F7-H6* | Sow | 130 | 0 | 2 NT-derived piglets born |
| O210 (1) | F7-H6 | Gilt | 115 | 0 | Return to estrus on day 26 |
| O193 (1) | F7-H6 | Sow | 146 | 0 | Return to estrus on day 26 |
| O218 (0) | F7-H6 | Sow | 86 | 0 | Return to estrus on day 33 |
| O176 (1) | F7-H6 | Gilt | 99 | 0 | Return to estrus on day 29 |
| O186 (0) | F9-J7 | Sow | 150 | 0 | Degenerated day 47-53 |
| O203 (1) | F9-J7* | Sow | 130 | 0 | Degenerated day 27-33 |
| O272 (0) | F9-J7 | Gilt | 56 | 0 | Return to estrus on day 22 |
| O265 (1) | F9-J7 | Sow | 124 | 0 | Return to estrus on day 26 |
| O291 (1) | F9-J7* | Sow | 92 | 0 | Return to estrus on day 28 |
| O227 (1) | F9-J7 | Sow | 94 | 0 | Return to estrus on day 25 |
| O221 (1) | F9-J7* | Sow | 110 | 0 | Return to estrus on day 26 |

To increase the likelihood of establishing a small litter of NT-derived piglets, transfer of reconstructed embryos was made to a mated surrogate. In the one embryo transfer performed in this group, the surrogate (O212) was mated on the first day of standing estrus and received NT-derived embryos the same day. Although any fertilized embryos would theoretically be 43-55 hours behind development of the transferred NT-derived embryos, the actual in vivo development rate for NT-derived embryos is unknown. Early pig embryos have a significantly lower rate of survival when present in a surrogate along with embryos at slightly more advanced stage. Thus, an apparent embryonic asynchrony may be advantageous should NT-derived embryos develop at a slower rate than naturally fertilized embryos. Seven piglets (4 females and 3 males) were delivered by cesarean section at term.

EXAMPLE 4

Transfer of NT-Derived Embryos to Unmated Surrogates

Twenty additional transfers of only NT-derived embryos to unmated surrogates were performed. Pregnancy was confirmed by ultrasound in six of these surrogates, with two continuing to cesarean section at term. Two live piglets were delivered from surrogate O230, one of which (O230-2) died from respiratory distress syndrome shortly after delivery. Four live piglets were delivered from surrogate O226, with one (O226-4) dying shortly after birth from respiratory distress syndrome.

EXAMPLE 5
Microsattelite and Genomic Targeting Analyses of Piglets

A total of 28 embryo transfers were performed. Microsatellite reactions were amplified using fluorescent primers kindly provided by the USDA supported U.S. Pig Genome Coordination Project and analyzed by Lark Technologies, Inc (Houston, Tex.). The microsatellite analysis revealed that 6 of 6 haplotypes for one female piglet (O212-2) from the mated surrogate were identical to that of the F7 fetal cell line from which knockout donor line F7-H6 was derived (Table 3). Furthermore, 3 of 6 haplotypes of O212-2 were not compatible with mating of the surrogate. All other piglets had at least 4 haplotype mismatches with the F7 line and were compatible with mating of the surrogate.

For the piglets from the unmated surrogates, microsatellite haplotypes of all 6 piglets from the two litters were identical to the F7 and F3 donor parental cell lines, respectively.

TABLE 3

Microsatellite analysis of donor miniature swine parental cell lines, offspring and surrogates.

| | SW957 | S0097 | S0155 | S0227 | S0216 | SW936 |
|---|---|---|---|---|---|---|
| F3 | 113/139 | 207 | 149 | 231 | 186 | 93/103 |
| O226-1 | 113/139 | 207 | 149 | 231 | 186 | 93/103 |
| O226-2 | 113/139 | 207 | 149 | 231 | 186 | 93/103 |
| O226-3 | 113/139 | 207 | 149 | 231 | 186 | 93/103 |
| O226-4 | 113/139 | 207 | ND | 231 | ND | 93/103 |
| O226 (SUR) | 113 | 207 | 155/161 | 231 | 186/214 | 97/103 |
| F7 | 113 | 207 | 149 | 231 | 186 | 93 |
| O230-1 | 113 | 207 | 149 | 231 | 186 | 93 |
| O230-2 | 113 | 207 | 149 | 231 | 186 | 93 |
| O212-2 | 113 | 207 | 149 | 231 | 186 | 93 |
| O212-1 | 113 | 207/209 | 161 | 231 | 214 | 95/103 |
| O212-3 | 113 | 209/237 | 161 | 231 | 214 | 95/103 |
| O212-4 | 113/141 | 209/237 | 161 | 231 | 214 | 95/103 |
| O212-5 | 113 | 209/237 | 161 | 231 | 214 | 95/103 |
| O212-6 | 113/141 | 209/237 | 161 | 231 | 214 | 95/103 |
| O212-7 | 113/141 | 207/209 | 161 | 231 | 214 | 95/103 |
| O230 (SUR) | 113/127 | 207/239 | 155/159 | 231 | 186/214 | 103/111 |

TABLE 3-continued

Microsatellite analysis of donor miniature swine parental cell lines, offspring and surrogates.

| | SW957 | S0097 | S0155 | S0227 | S0216 | SW936 |
|---|---|---|---|---|---|---|
| O212 (SUR) | 113/141 | 207/237 | 161 | 231 | 214 | 95/103 |

Allele sizes, in base pairs, are indicated for the six markers.
SUR, surrogate animal.
ND, not determined.

Figure 2A:
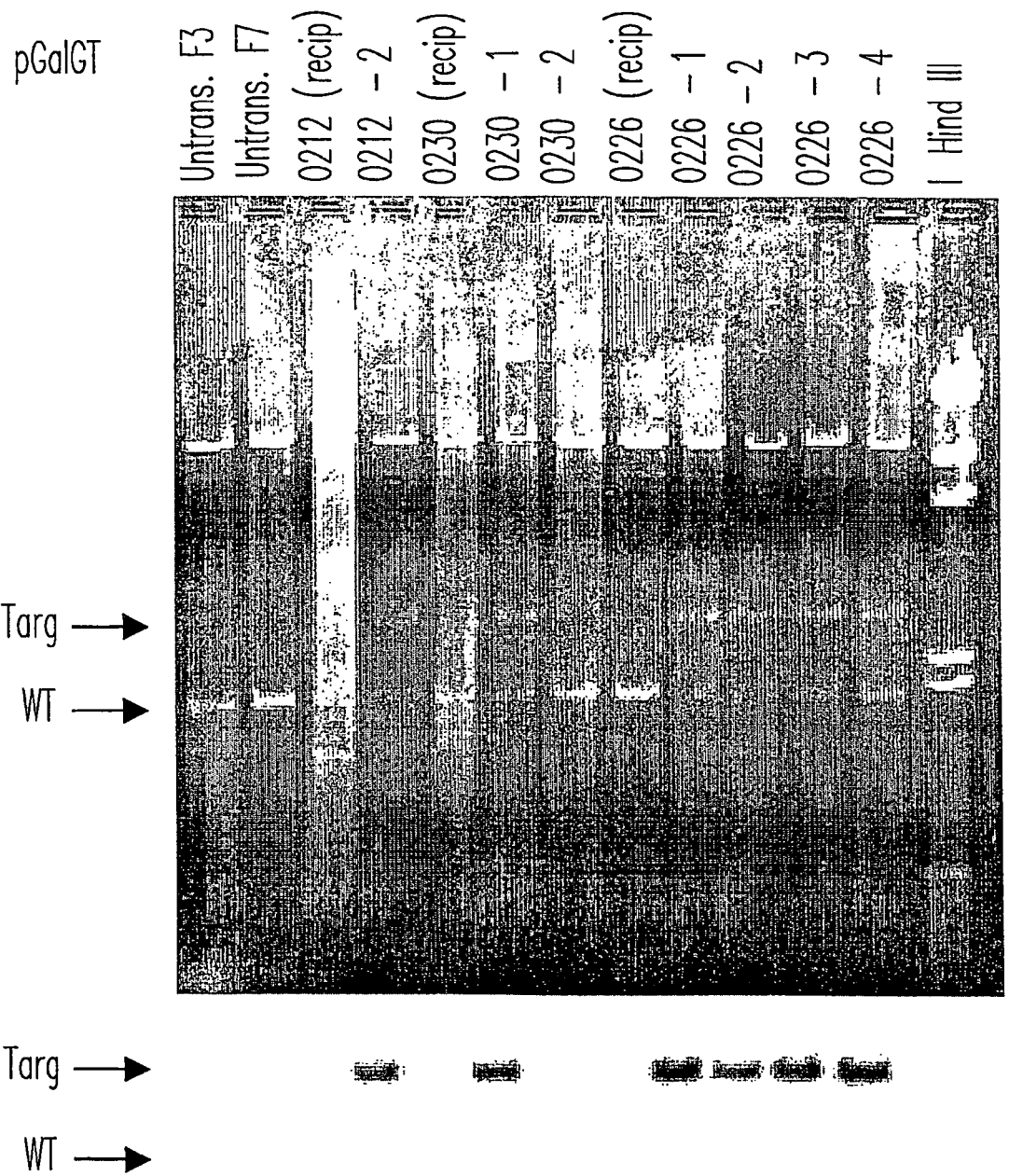
FIG. 2. Targeting analysis of NT-derived piglets, parental miniature swine fetal cell lines F3 and F7, and surrogate sows (SUR). Refer to FIG. 1 for a diagrammatic description of the assays. Panel A, upstream genomic PCR analysis with primers F238 and R823. Panel B, downstream genomic PCR analysis with primers F527 and GR2520. Following transfer, digested reactions were probed with an oligonucleotide (Bip419) from the IRES portion of the selection cassette. The analysis of all offspring, with the exception of O230-2, is consistent with a replacement-type targeting event at one GGTA1 allele.
Figure 2B:
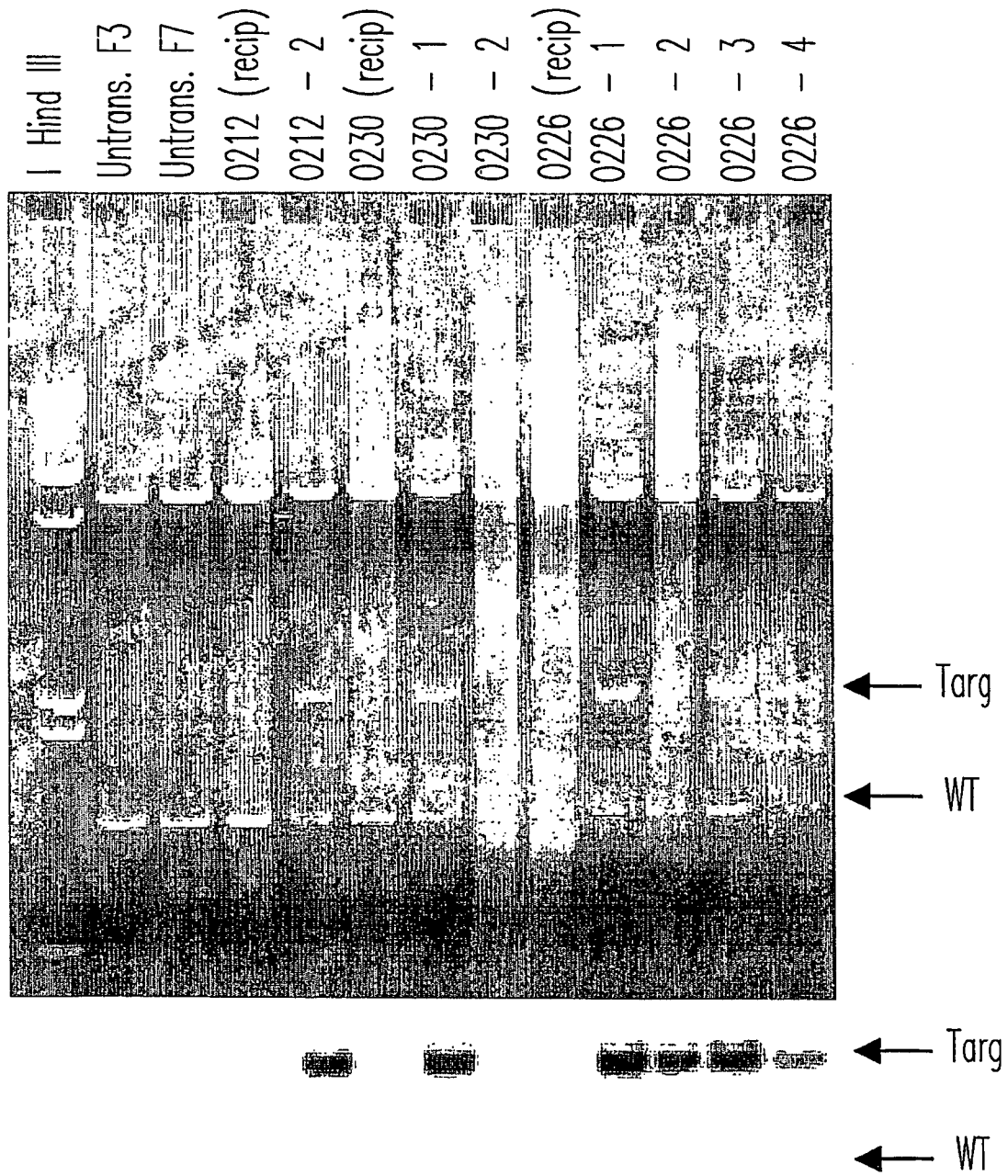
Figure 3:
FIG. 3. A photograph of piglet O230-1, taken at 10 days of age

Genomic targeting analysis was performed on DNA samples from all NT-derived piglets, the untransfected F3 and F7 donor parental cell lines, and surrogates (FIG. 2). For all piglets except O230-2, analysis of both ends of the GGTA1 locus revealed the presence of one replacement-type targeted allele.

EXAMPLE 6

Health Evaluation of Knockout Piglets

A health summary for the seven NT-derived piglets is presented in Table 4. Four of the five piglets surviving beyond the immediate postpartum period remain healthy, with a normal growth rate for miniature swine. The fifth, O226-3, died suddenly at 17 days of age during a routine blood draw. Necropsy revealed a dilated right ventricle and thickening of the heart wall. Based on this finding, and development of mild abdominal distension in O230-1, the four remaining pigs underwent cardiac exam by Doppler echocardiography. There were no exceptional findings for piglets O212-2 and O226-1. O226-2 displayed a low velocity regurgitation at the center of the tricuspid valve that may be inconsequential. However, an enlarged pulmonary artery with moderate pulmonary hypertension was noted in O230-1. Radiography also revealed an enlargement of the right side of the heart. Although this animal is active and shows no signs of distress, its long-term outlook is questionable.

A number of other abnormalities were noted at birth among surviving piglets, none of which appear to affect the overall health and well being of the animals. The most common of these was a flexure deformity of the distal interphalangeal joint, corrected by physical therapy and, in one case, by temporary splinting of the hind limb. Given the lack of a consistent phenotype among the NT-derived piglets reported here, and the fact that only one GGTA1 allele has been targeted, it is unlikely that the abnormalities we have seen are related to the genetic modification, but rather are the result of improperly reprogrammed epigenetic factors. With the exception of O212-2, the 4 surviving piglets were somewhat undersized, with birth weights of 450-650 g (strain average 860 g). Despite being among a litter containing 6 normal commercial piglets, the birth weight of O212-2 was by far the largest of the NT-derived miniature swine piglets at 1100 g.

The significance of this observation is not yet clear.

TABLE 4

Health Summary of NT-derived Miniature Swine Piglets.

| Piglet | Physical Findings | Birth Weight | Clinical Symptoms/Cardiac Exam Findings | Status |
|---|---|---|---|---|
| O212-2 | One eye, small ear flaps with no patent ear canals. | 1100 g | No clinical symptoms. No significant echocardiogram findings. | Healthy Normal growth |
| O230-1 | Flexure deformity of distal interphalangeal joint at birth (responded to physical therapy). | 450 g | Mild abdominal ascities. Right ventricular enlargement and pulmonary hypertension. | Normal growth |
| O230-2 | Flexure deformity of distal interphalangeal joint at birth. Dysmaturity at birth. | 115 g | Died shortly following delivery of respiratory distress syndrome. No gross lesions observed at necropsy. | Dead |
| O226-1 | Normal | 600 g | No clinical symptoms. No significant echocardiogram findings. | Healthy Normal growth |
| O226-2 | Flexure deformity of distal interphalangeal joint at birth (responded to physical therapy and splinting). | 650 g | No clinical symptoms. Low velocity regurgitation at center of tricuspid valve. | Healthy Normal growth |
| O226-3 | Flexure deformity of distal interphalangeal joint at birth (responded to physical therapy). | 550 g | Death during routine blood draw 17 days after birth. Dilated right ventricle with thickening of heart wall observed at necropsy. | Dead |
| O226-4 | Cleft palate. Dysmaturity at birth. | 250 g | Died shortly following delivery of respiratory distress syndrome. No gross lesions observed at necropsy. | Dead |

EXAMPLE 7

Production of Live GGTA1 Knockout Pigs

Five different knockout male cell lines were used for nuclear transfer (in vitro matured sow oocytes as recipient cells), and resulting embryos were transferred to fourteen different surrogates. Nine surrogates had established a pregnancy as determined by ultrasound. One pregnancy was terminated at day 31 and seven fetuses were recovered (3 appeared normal and 4 appeared to be degenerating). Six pregnancies disappeared by day 41. From one surrogate (#O098) a viable male piglet was recovered. A stillborn male piglet was recovered from the same surrogate. An additional piglet died shortly after recovery from #O100 on Jul. 12, 2002. The live male piglet was confirmed to have the GGTA1 gene altered as predicted and is a healthy animal.

What is claimed is:

1. A knockout swine whose genome comprises a disrupted α(1,3)-galactosyltransferase gene, wherein expression of functional α(1,3)-galactosyltransferase in the knockout swine is decreased as compared to a wild-type swine and tissue from the swine exhibits decreased hyperacute rejection as compared to a wild-type swine tissue.

2. The swine of claim 1, wherein the wild-type α(1,3)-galactosyltransferase gene encodes SEQ ID NO: 1.

3. The swine of claim 1, having a reduced amount α(1,3)-galactosyl epitope on the surface of at least some cells, as compared to a wild-type swine.

4. An isolated swine organ comprising cells, the genome of which comprise a disrupted α(1,3)-galactosyltransferase gene, wherein expression of functional α(1,3)-galactosyltransferase in the isolated organ is decreased as compared to a wild-type organ and wherein the organ exhibits decreased hyperacute rejection as compared to a wild-type swine organ.

5. The isolated organ of claim 4, wherein the wild-type α(1,3)-galactosyltransferase gene encodes SEQ ID NO: 1.

6. The isolated organ of claim 4 wherein the organ is selected from a group consisting of heart, liver, kidney, pancreas, lung, thyroid and skin.

7. The isolated organ of claim 4, having a reduced amount α(1,3)-galactosyltransferase epitope on the surface of at least some cells, as compared to cells from a wild-type swine organ.

8. A method for producing a transgenic swine embryo, comprising:
   (a) enucleating a swine oocyte;
   (b) fusing the oocyte with a donor swine fibroblast cell the genome of which comprises a disrupted α(1,3)-galactosyltransferase gene; and
   (c) activating the oocyte to produce a transgenic swine embryo whose genome comprises a disrupted α(1,3)-galactosyltransferase gene, said embryo being capable of producing a transgenic swine of claim 1.

9. A method for producing a knockout swine comprising:
(a) enucleating a swine oocyte;
(b) fusing the oocyte with a donor swine fibroblast cell the genome of which comprises a disrupted α(1,3)-galactosyltransferase gene;
(c) activating the oocyte to produce an embryo; and
(d) implanting the embryo into a surrogate swine, wherein the surrogate swine has initiated estrus, but has not yet completed ovulation, for term delivery to produce a knockout swine whose genome comprises a disrupted α(1,3)-galactosyltransferase gene, wherein expression of functional α(1,3)-galactosyltransferase in the knockout swine is decreased as compared to a wild-type swine, and tissue from the swine exhibits decreased hyperacute rejection as compared to a wild-type swine tissue.

10. The method of claim 8 or 9, wherein the wild-type α(1,3)-galactosyltransferase comprises SEQ ID NO:1.

11. A swine embryo produced according to claim 8.

12. An isolated swine organ derived from the embryo of claim 11 wherein the organ exhibits decreased hyperacute rejection as compared to a wild-type swine organ.

13. An isolated swine tissue derived from the embryo of claim 11 wherein the tissue exhibits decreased hyperacute rejection as compared to a wild-type swine tissue.

14. An isolated tissue derived from the swine of claim 1 wherein the tissue exhibits decreased hyperacute rejection as compared to a wild-type swine tissue.

15. A progeny swine of the swine of claim 1, wherein said progeny swine comprises a genome comprising a disrupted α(1,3)-galactosyltransferase gene and tissue from the progeny exhibits decreased hyperacute rejection as compared to a wild-type swine tissue.

16. A gamete derived from the swine of claim 1 or 15, wherein said gamete comprises a genome comprising a disrupted α(1,3)-galactosyltransferase gene and tissue from swine produced by said gamete exhibits decreased hyperacute rejection as compared to a wild-type swine tissue.

17. The gamete of claim 16, which is a sperm.

18. The gamete of claim 16, which is an ovum.

* * * * *

UNITED STATES PATENT AND TRADEMARK OFFICE
CERTIFICATE OF CORRECTION

| | | |
|---|---|---|
| PATENT NO. | : 7,547,816 B2 | Page 1 of 1 |
| APPLICATION NO. | : 10/499407 | |
| DATED | : June 16, 2009 | |
| INVENTOR(S) | : Day et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this

Fourteenth Day of December, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 371
<212> TYPE: PRT
<213> ORGANISM: Sus scrofa

<400> SEQUENCE: 1
```

```
Met Asn Val Lys Gly Arg Val Val Leu Ser Met Leu Val Ser Thr
 1               5                  10                  15

Val Met Val Val Phe Trp Glu Tyr Ile Asn Ser Pro Glu Gly Ser Leu
             20                  25                  30

Phe Trp Ile Tyr Gln Ser Lys Asn Pro Glu Val Gly Ser Ser Ala Gln
         35                  40                  45

Arg Gly Trp Trp Phe Pro Ser Trp Phe Asn Asn Gly Thr His Ser Tyr
     50                  55                  60

His Glu Glu Glu Asp Ala Ile Gly Asn Glu Lys Glu Gln Arg Lys Glu
 65                  70                  75                  80

Asp Asn Arg Gly Glu Leu Pro Leu Val Asp Trp Phe Asn Pro Glu Lys
                 85                  90                  95

Arg Pro Glu Val Val Thr Ile Thr Arg Trp Lys Ala Pro Val Val Trp
             100                 105                 110

Glu Gly Thr Tyr Asn Arg Ala Val Leu Asp Asn Tyr Tyr Ala Lys Gln
         115                 120                 125

Lys Ile Thr Val Gly Leu Thr Val Phe Ala Val Gly Arg Tyr Ile Glu
130                 135                 140

His Tyr Leu Glu Glu Phe Leu Ile Ser Ala Asn Thr Tyr Phe Met Val
145                 150                 155                 160

Gly His Lys Val Ile Phe Tyr Ile Met Val Asp Asp Ile Ser Arg Met
                 165                 170                 175

Pro Leu Ile Glu Leu Gly Pro Leu Arg Ser Phe Lys Val Phe Glu Ile
             180                 185                 190

Lys Ser Glu Lys Arg Trp Gln Asp Ile Ser Met Met Arg Met Lys Thr
         195                 200                 205

Ile Gly Glu His Ile Leu Ala His Ile Gln His Glu Val Asp Phe Leu
210                 215                 220

Phe Cys Met Asp Val Asp Gln Val Phe Gln Asn Asn Phe Gly Val Glu
225                 230                 235                 240

Thr Leu Gly Gln Ser Val Ala Gln Leu Gln Ala Trp Trp Tyr Lys Ala
                 245                 250                 255

His Pro Asp Glu Phe Thr Tyr Glu Arg Arg Lys Glu Ser Ala Ala Tyr
             260                 265                 270

Ile Pro Phe Gly Gln Gly Asp Phe Tyr Tyr His Ala Ala Ile Phe Gly
         275                 280                 285

Gly Thr Pro Thr Gln Val Leu Asn Ile Thr Gln Glu Cys Phe Lys Gly
290                 295                 300

Ile Leu Gln Asp Lys Glu Asn Asp Ile Glu Ala Glu Trp His Asp Glu
305                 310                 315                 320

Ser His Leu Asn Lys Tyr Phe Leu Leu Asn Lys Pro Thr Lys Ile Leu
                 325                 330                 335

Ser Pro Glu Tyr Cys Trp Asp Tyr His Ile Gly Met Ser Val Asp Ile
             340                 345                 350

Arg Ile Val Lys Ile Ala Trp Gln Lys Lys Glu Tyr Asn Leu Val Arg
         355                 360                 365

Asn Asn Ile
370

<210> SEQ ID NO 2
<211> LENGTH: 1269
<212> TYPE: DNA
<213> ORGANISM: Sus scrofa
```

```
<400> SEQUENCE: 2
catgaggaga aaataatgaa tgtcaaagga agagtggttc tgtcaatgct gcttgtctca    60
actgtaatgg ttgtgttttg ggaatacatc aacagcccag aaggttcttt gttctggata   120
taccagtcaa aaacccaga agttggcagc agtgctcaga ggggctggtg gtttccgagc    180
tggtttaaca atgggactca cagttaccac gaagaagaag acgctatagg caacgaaaag   240
gaacaaagaa aagaagacaa cagaggagag cttccgctag tggactggtt taatcctgag   300
aaacgcccag aggtcgtgac cataaccaga tggaaggctc cagtggtatg ggaaggcact   360
tacaacagag ccgtcttaga taattattat gccaaacaga aaattaccgt gggcttgacg   420 gttttttgctg tcggaagata cattgagcat tacttggagg agttcttaat atctgcaaat   480
acatacttca tggttggcca caaagtcatc ttttacatca tggtggatga tatctccagg   540
atgcctttga tagagctggg tcctctgcgt tcctttaaag tgtttgagat caagtccgag   600
aagaggtggc aagacatcag catgatgcgc atgaagacca tcggggagca catcctggcc   660
cacatccagc acgaggtgga cttcctcttc tgcatggacg tggatcaggt cttccaaaac   720
aactttgggg tggagaccct gggccagtcg gtggctcagc tacaggcctg gtggtacaag   780
gcacatcctg acgagttcac ctacgagagg cggaaggagt ccgcagccta cattccgttt   840
ggccagggga ttttttatta ccacgcagcc attttttgggg gaaacacccac tcaggttcta   900 aacatcactc aggagtgctt caagggaatc ctccaggaca aggaaaatga catagaagcc   960
gagtggcatg atgaaagcca tctaaacaag tatttccttc tcaacaaacc cactaaaatc  1020
ttatccccag aatactgctg ggattatcat ataggcatgt ctgtggatat taggattgtc  1080
aagatagctt ggcagaaaaa agagtataat ttggttagaa ataacatctg actttaaatt  1140
gtgccagcag tttctgaat ttgaaagagt attactctgg ctacttcctc agagaagtag  1200
cacttaattt taacttttaa aaaaatacta acaaaatacc aacacagtaa gtacatatta  1260
ttcttccctt                                                         1269

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
acaacagagg agagcttccg                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctctcacact cgcgaaacac                                               20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
```

```
ggtcgtgacc ataaccagat g                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ttaccacgaa gaagaagacg c                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aggatgtgcc ttgtaccacc                                                20

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ggttggccac aaagtcatc                                                 19

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cactatttgg aggacagggt c                                              21
```